US006228843B1

(12) United States Patent
Dempsey

(10) Patent No.: US 6,228,843 B1
(45) Date of Patent: May 8, 2001

(54) METHOD OF USING PKC INHIBITING COMPOUNDS TO TREAT VASCULAR DISEASE

(75) Inventor: Edward C. Dempsey, Denver, CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/557,038

(22) Filed: Apr. 21, 2000

Related U.S. Application Data

(60) Provisional application No. 60/130,916, filed on Apr. 23, 1999.

(51) Int. Cl.$^7$ ..................................................... A01N 43/04
(52) U.S. Cl. ................................................................ 514/31
(58) Field of Search ................................................ 514/31

(56) References Cited

U.S. PATENT DOCUMENTS

| | | | |
|---|---|---|---|
| 5,189,046 | 2/1993 | Burch et al. | 514/330 |
| 5,763,441 | 6/1998 | App et al. | 514/249 |
| 5,792,752 | 8/1998 | Cho-Chung et al. | 514/47 |
| 5,792,771 | 8/1998 | App et al. | 514/259 |
| 5,886,195 | 3/1999 | Tang et al. | 549/75 |
| 5,932,422 | 8/1999 | Shyjan et al. | 435/6 |
| 5,981,569 | 11/1999 | App et al. | 514/419 |

OTHER PUBLICATIONS

Dempsey et al., Can. J. Physiol. Pharmacol., 75(7), 936–944 (abstract), 1997.*
Asiedu et al., *Cancer Research*, vol. 55, pp. 3716–2720 (Sep. 1, 1995).
Bear et al., *Anti–Cancer Drugs*, vol. 7, pp. 299–306 (1996).
Bodily et al., *Cancer Letters*, vol. 136, pp. 67–74 (1999).
Carr, Jr. et al., *Anti–Cancer Drugs*, vol. 6, pp. 384–391 (1995).
Chelliah et al., *Biochemical Pharmacology*, vol. 54, pp. 563–573 (1997).
Davis et al., *Journal of Cellular Biochemistry*, vol. 65, pp. 308–324 (1997).
Dräger et al., *Leukemia*, vol. 13, pp. 62–69 (1999).
Ekinci et al. *Int. J. Devl Neuroscience*, vol. 15, No. 7, pp. 867–874 (1997).
Farokhzad et al., *Surgery*, vol. 124, No. 2, pp. 380–387 (Aug., 1998).
Grant et al., *Clinical Cancer Research*, vol. 4, Issue 3, pp. 611–618 (1998).
Hickman et al., *British Journal of Cancer*, vol. 72, Issue 4, pp. 998–1003 (1995).
Jayson et al. *British Journal of Cancer*, vol. 72, Issue 2, pp. 461–468 (1995).
Katanietz et al., *Molecular Pharmacology*, vol. 46, pp. 374–379 (1994).
Khan et al., *Journal of Chromatography B*, vol. 709, pp. 113–117 (1998).
Kitada, *British Journal of Haematology*, vol. 106, pp. 995–1004 (1999).
Lee et al., *Molecular Pharmacology*, vol. 51, pp. 439–447 (1997).
Li, *Leukemia Research*, vol. 21, No. 5, pp. 391–397 (1997).
Lilly et al., *Experimental Hematology*, vol. 24, pp. 613–621 (1996).
Liu et al., *Leukemia*, vol. 13, pp. 1273–1280 (1999).
Lorenzo et al., *Cancer Research*, vol. 59, pp. 6137–6144 (Dec. 15, 1999).
Lorenzo et al., *The Journal of Biological Chemistry*, vol. 272, No. 52, pp. 33338–33343 (1997).
Malarkey et al., *Cell Signal*, vol. 8, No. 2, pp. 123–129 (1996).
Matthews et al., *The Journal of Biological Chemistry*, vol. 272, No. 32, pp. 20245–20250 (1997).
May et al., *The Journal of Biological Chemistry*, vol. 269, No. 43, pp. 26865–26870 (1994).
McGown et al., *British Journal of Cancer*, vol. 77(2), pp. 216–220, (1998).
Mohammad et al., *Leukemia Research*, vol. 19, pp. 667–673 (1995).
Mohammad et al., *Clinical Cancer Research*, vol. 4, pp. 445–453 (Feb. 1998).
Mohammad et al., *Clinical Cancer Research*, vol. 4, pp. 1337–1343 (May, 1998).
Prendiville et al., *British Journal of Cancer*, vol. 70, Issue 4, pp. 573–578 (1994).
Sista et al., *Molecular and Cellular Biochemistry*, vol. 141, pp. 129–134 (1994).
Slater et al., *The Journal of Biological Chemistry*, vol. 273, No. 36, pp. 23160–23168 (1998).
Song et al., *Leukemia*, vol. 13, pp. 275–281 (1999).
Song et al., *The Journal of Biological Chemistry*, vol. 274, No. 3, pp. 1677–1682 (1999).
Steube et al., *Biochemical and Biophysical Research Communications*, vol. 214, No. 3, pp. 1197–1203 (Sep. 25, 1995).
Szallasi et al., *Molecular Pharmacology*, vol. 4, pp. 840–850 (1994).
Szallasi et al., *Cancer Research*, vol. 56, pp. 2105–2111 (1996).

(List continued on next page.)

*Primary Examiner*—Phyllis G. Spivack
(74) *Attorney, Agent, or Firm*—Sheridan Ross P.C.

(57) ABSTRACT

A method for treating pulmonary and systemic vascular diseases associated with cardiac hypotrophy, dysfunction or failure that involves the administration of an effective amount of a PKC antagonist to a patient suffering from one of such diseases is disclosed. PKC antagonists are selected from bryostatin derivatives and more preferably from bryostatin-1. The disease states treatable in accordance with the present invention are characterized by alterations in vascular structure, vascular tone, myocardial hypotrophy, dysfunction or failure, idiopathic pulmonary hypertension and chronic hypoxic pulmonary hypertension. Particular formulations include bryostatin-1 in an effective amount to treat one or more of the above-referenced diseases.

13 Claims, 15 Drawing Sheets

OTHER PUBLICATIONS

Taylor et al., *Cancer Research*, vol. 57, pp. 2468–2473 (1997).

Thijsen et al., *British Journal of Cancer*, vol. 79, pp. 1406–1412 (1999).

Varterasian et al., *Journal of Clinical Oncology*, vol. 16, No. 1, pp. 56–62 (1998).

Vrana et al., *Differentiation*, vol. 63, pp. 33–42 (1998).

Vrana et al., *International Journal of Oncology*, vol. 12, pp. 927–934 (1998).

Vrana et al., *Leukemia*, vol. 13, pp. 1046–1055, (1999).

Wall et al., *Leukemia Research*, vol. 23, pp. 881–888 (1999).

Wall et al., *Biochemical and Biophysical Research Communications*, vol. 266, pp. 76–80 (1999).

Wang et al., *Leukemia*, vol. 13, pp. 1564–1573 (1999).

Wang et al., *Biochemical Pharmacology*, vol. 56, pp. 635–644 (1998).

Watson et al., *Int. J. Radiat. Biol*, vol. 69, pp. 183–192 (1996).

Weitman et al., *Clinical Cancer Research*, vol. 5, pp. 2344–2348 (1999).

Wender et al., *Proc. Natl. Acad. Sci USA*, vol. 95, pp. 6624–6629 (1998).

Wender et al., *Med. Res Rev.*, vol. 5, pp. 388–407 (1999).

Zhang et al., *Cancer Research*, vol. 56, Issue 4, pp. 802–808 (1996).

\* cited by examiner

Chronic Hypoxic Pulmonary Hypertension (PHTN)
Abnormalities of Vascular Tone
- excessive contraction
- impaired vasodilation
*Structural Changes*
- hypertrophy
- proliferation
- matrix deposition
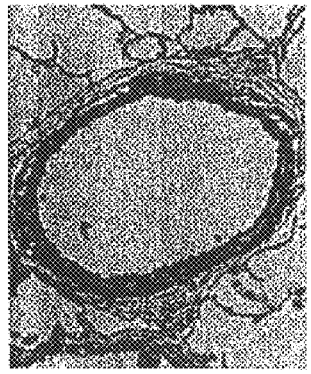 Hypoxia → 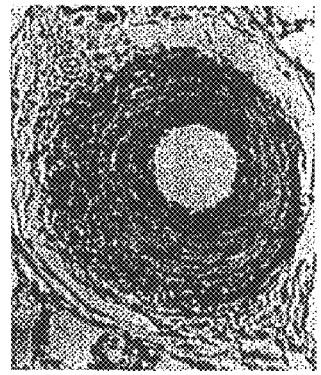
Fig # 1

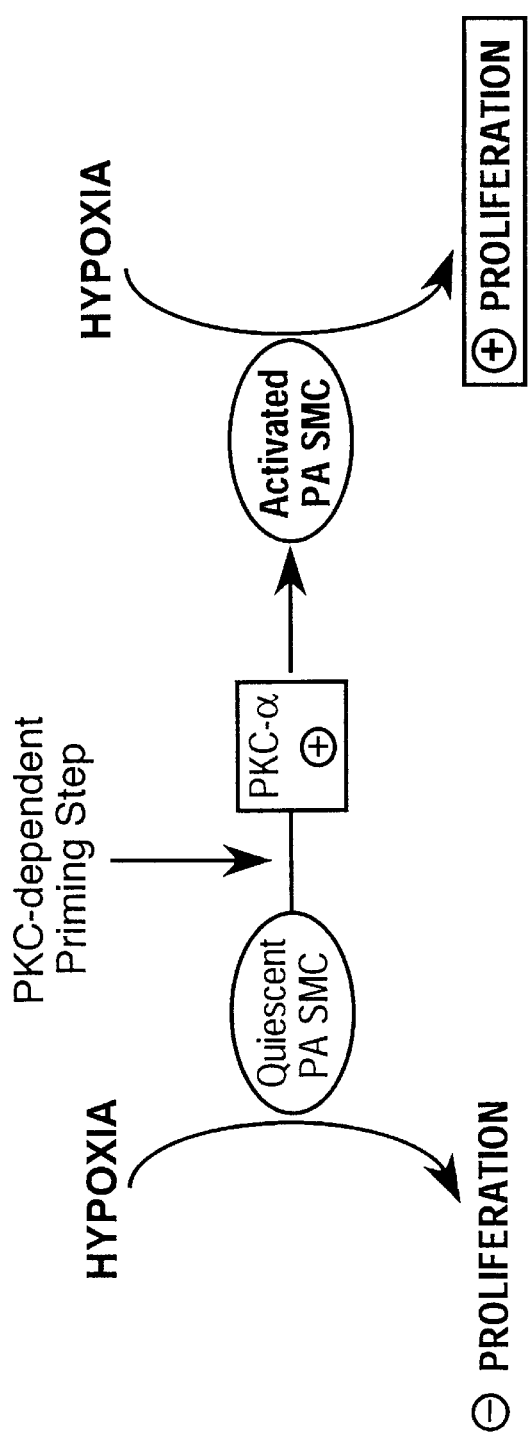

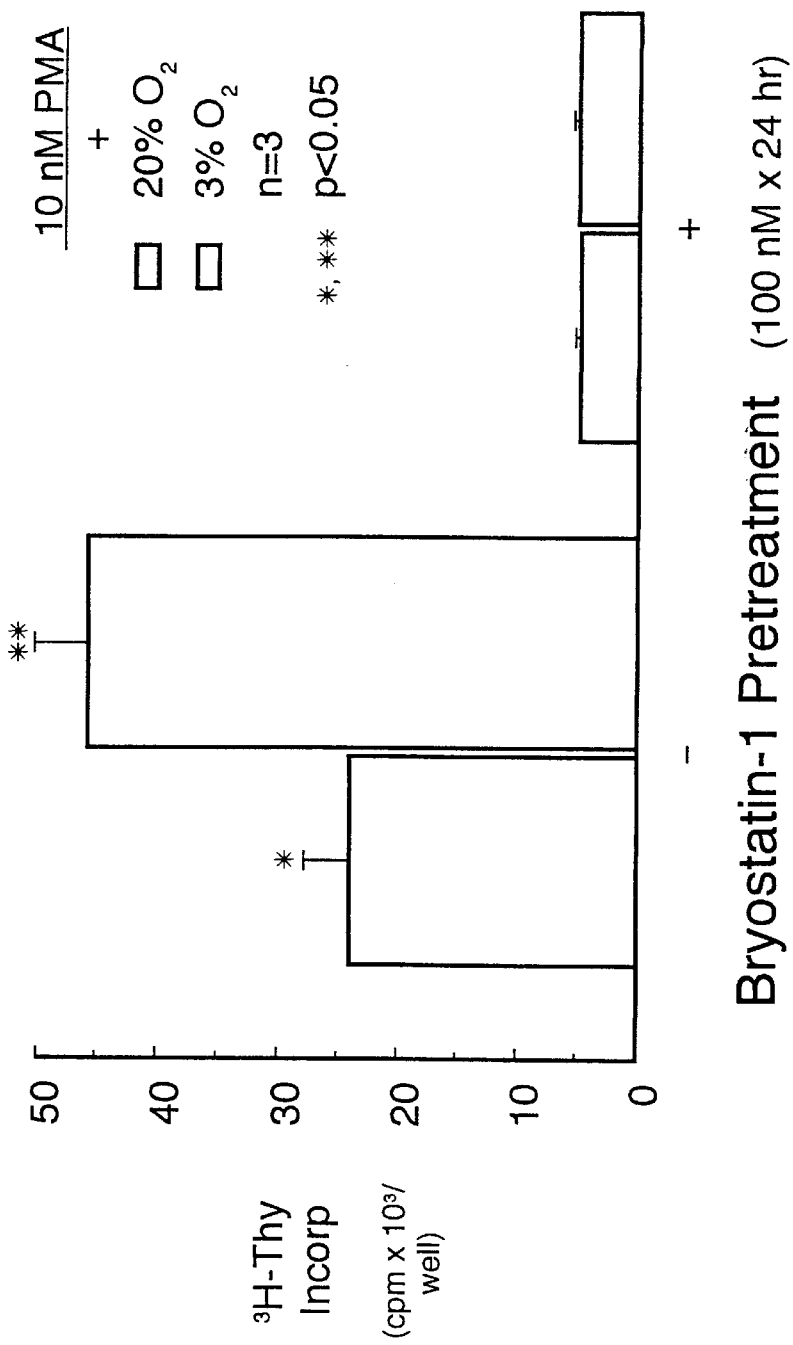
Fig #3

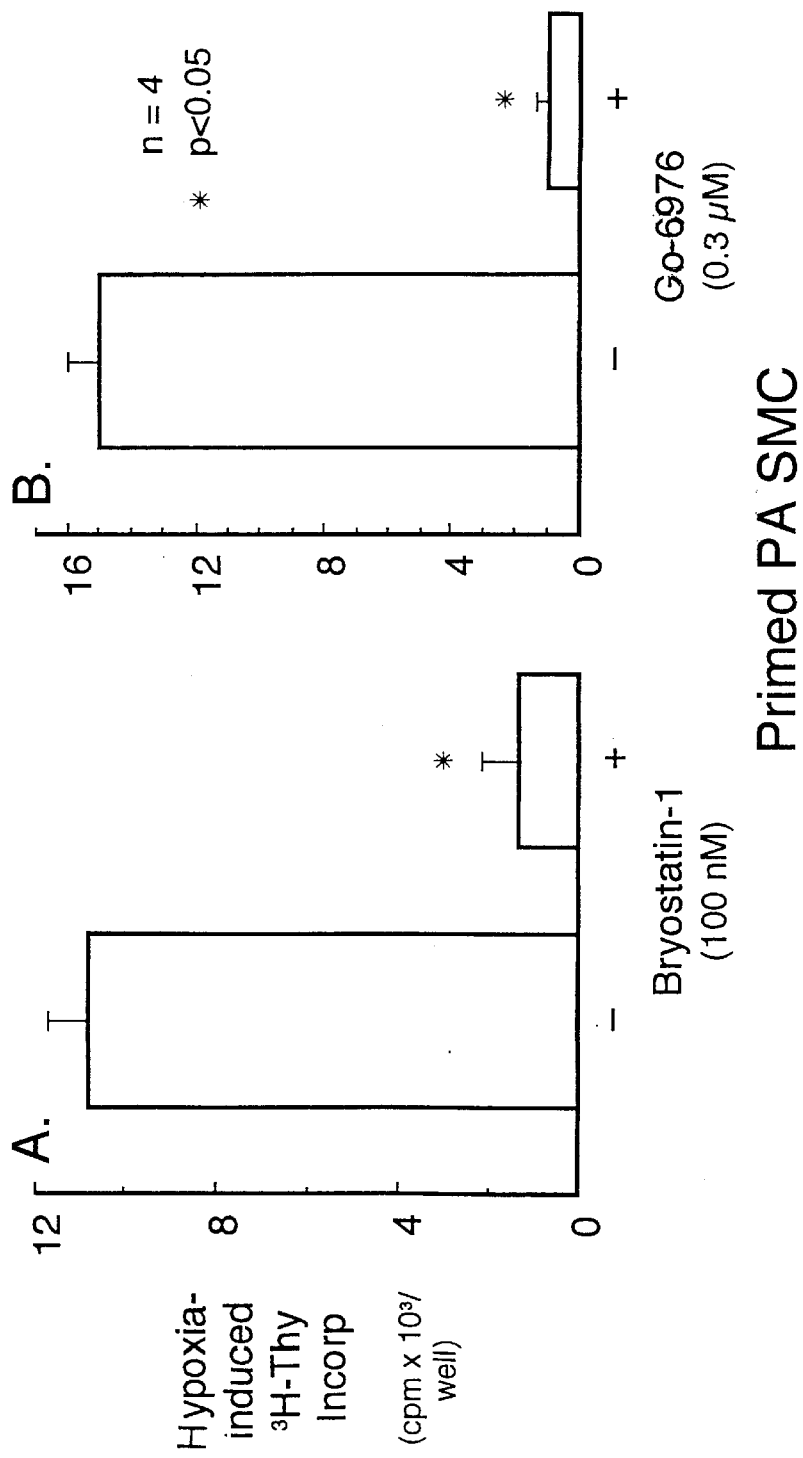

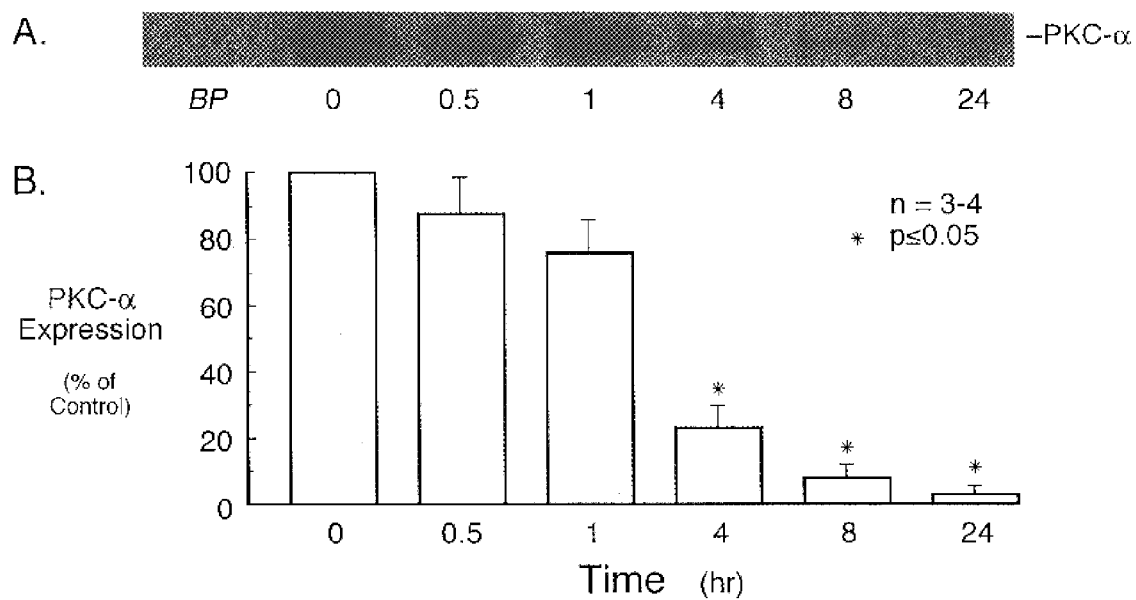
Fig #5

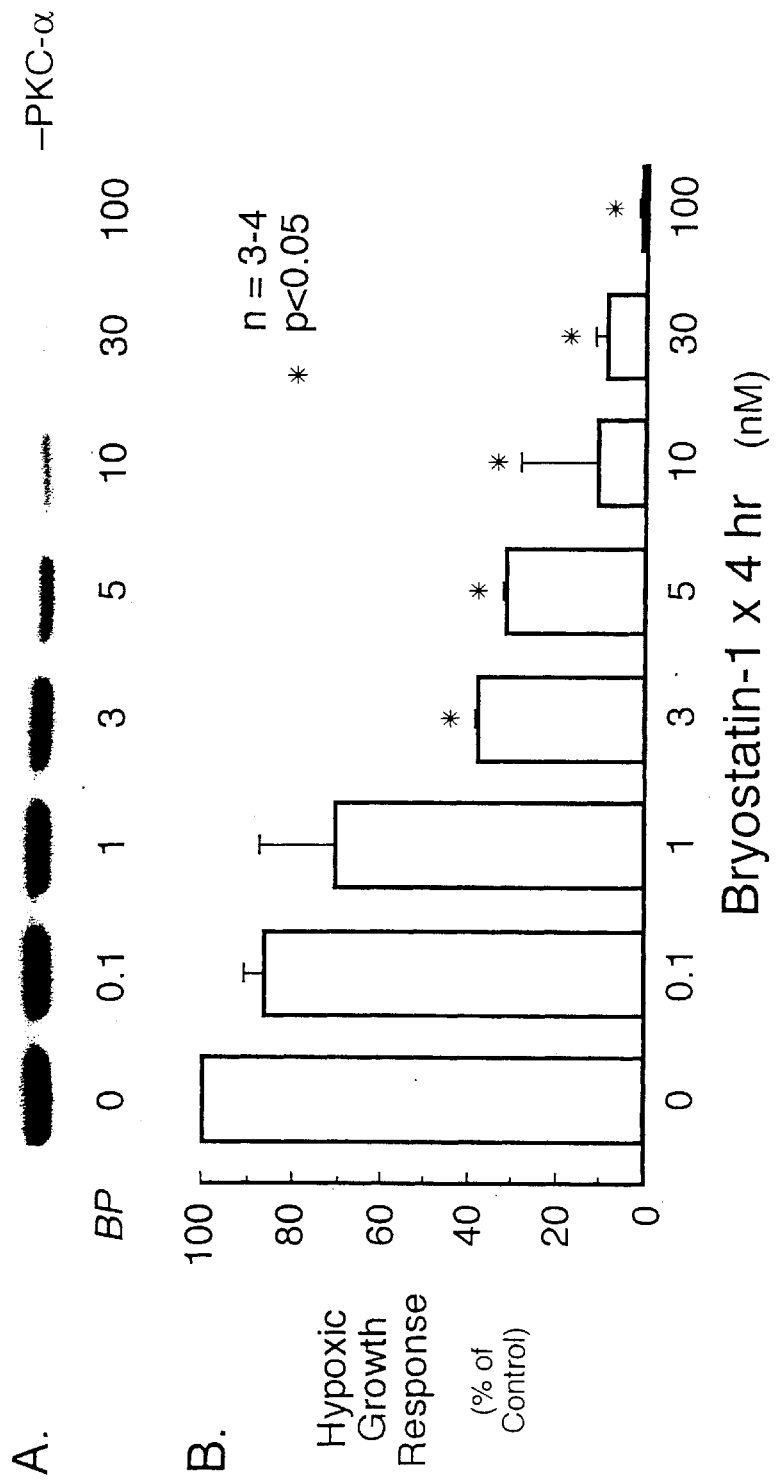

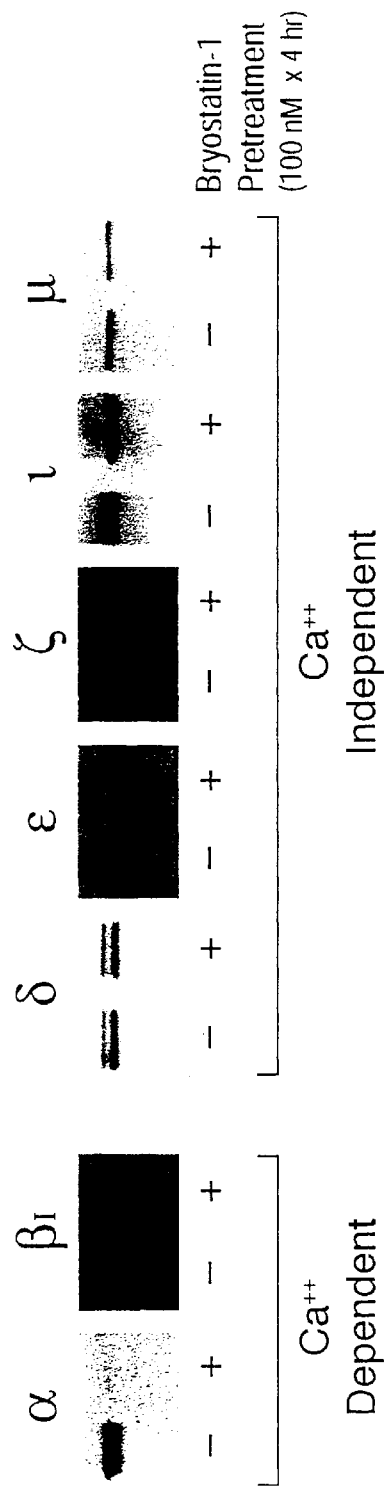

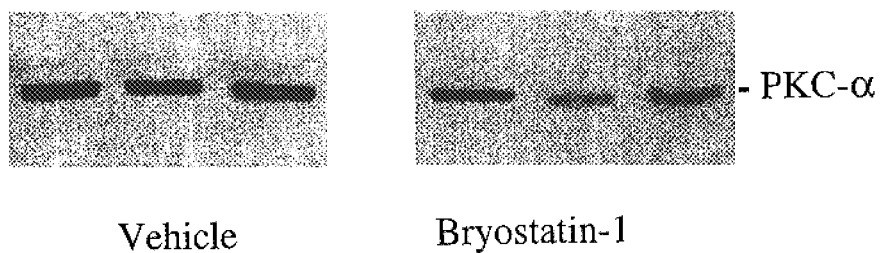
Figure 8: Chronic treatment with Bryostatin-1 decreases PKC-α protein levels in whole lung homogenates. Bryostatin given to adult ICR mice at dose of 11µg/kg/d for four weeks. PKC-α specific antibody used for Western Blot. Each lane represents a lung sample from a different adult ICR mouse.

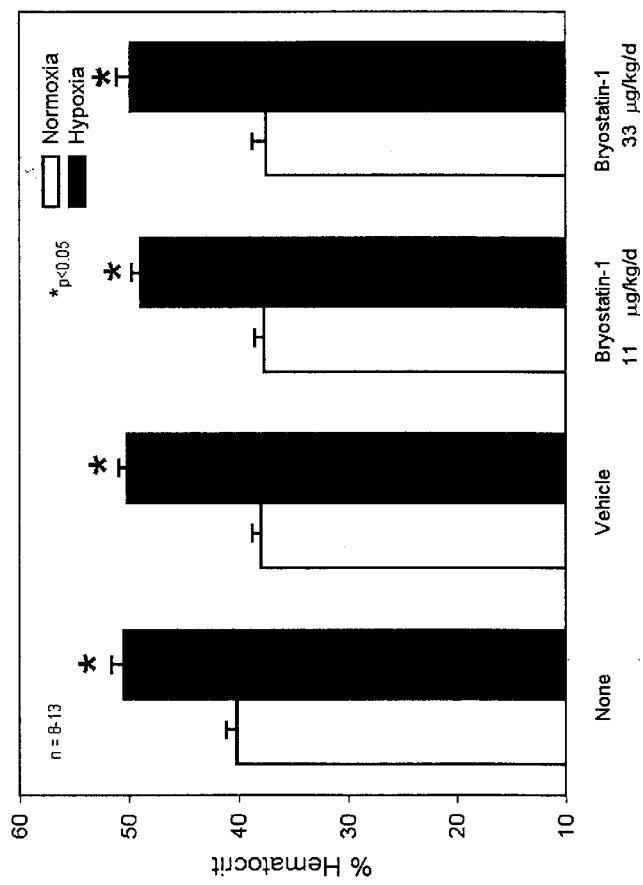

Figure 9: Hematocrit levels in response to chronic hypoxia and Bryostatin-1 administration. Chronic hypoxia induces a rise in hematocrit in this mouse model. Bryostatin-1 does not alter that polycythemic response. Blood samples were taken from mice exposed to normoxia or hypoxia and treated with nothing, vehicle (30% DMSO) or Bryostatin-1 (11- or 33-mg/kg/d) and were analyzed for hematocrit levels using capillary tubes and a standard technique. (☐ Normoxia, ■ Hypoxia). *$p \leq 0.05$ for all hypoxia vs. normoxia comparisons; N=8-13 for all groups.

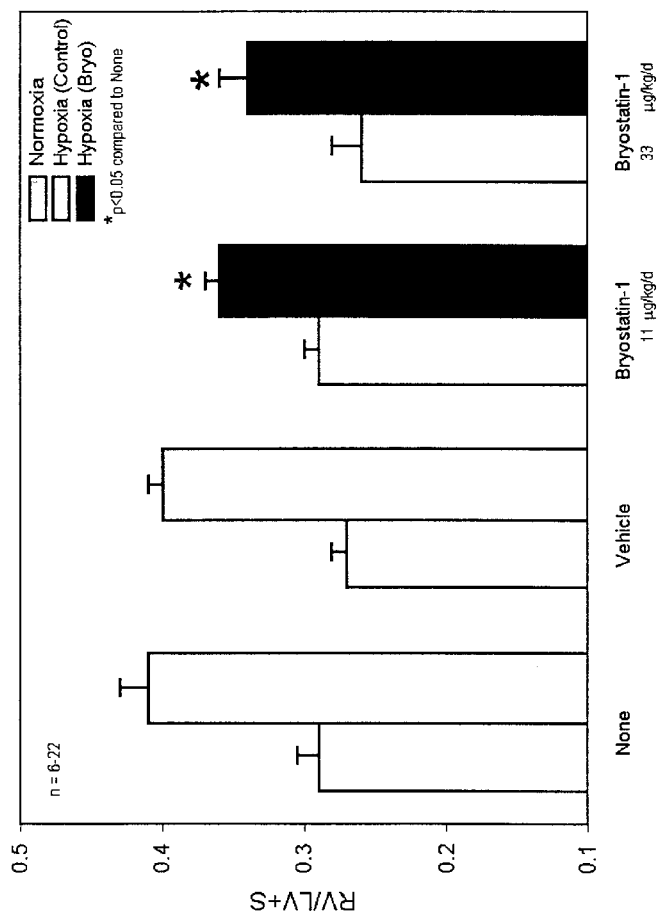

Figure 10: Chronic treatment with Bryostatin-1 attenuates hypoxia induced right ventricular hypertrophy. Ratio of right ventricular weight to left ventricular weight plus septum (RV/LV+S) is an index of right ventricular hypertrophy (RVH). RV/LV+S measurements were performed on mice exposed to either normoxia or hypoxia and treated with nothing, vehicle (30% DMSO), or Bryostatin-1 at 11- or 33-μg/kg/d. (☐ Normoxia for all groups, ■ Hypoxia for control groups, ■ Hypoxia for Bryostain-1 groups). *$p \leq 0.05$ as compared to no treatment; N=6-22 for each group.

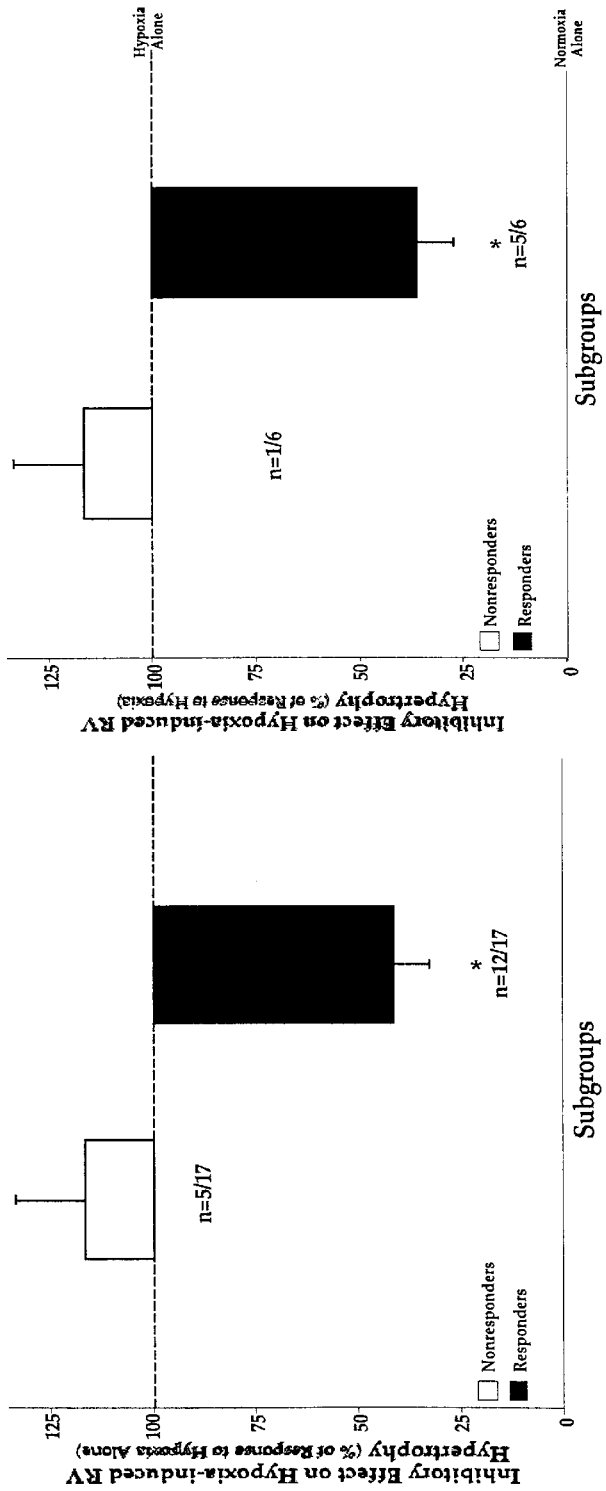

Figure 11: Subgroup analysis reveals a more marked attenuating effect of bryostatin-1 on hypoxia-induced right ventricular hypertrophy in a large subgroup of adult ICR mice. Results for either dose of bryostatin-1 on right ventricular hypertrophy clustered into nonresponder and responder (67% responder incidence for 11μg/kg/d dose and 83% responder incidence for 33μg/kg/d dose) subgroups. * $p<0.05$. The magnitude of the maximal inhibitory effect observed here is substantial when compared to previous studies with adult mouse and rat models and other compounds. The lack of a response of an occasional mouse may be due to limitations of chronic drug delivery and measurement of endpoints in such a small animal model.

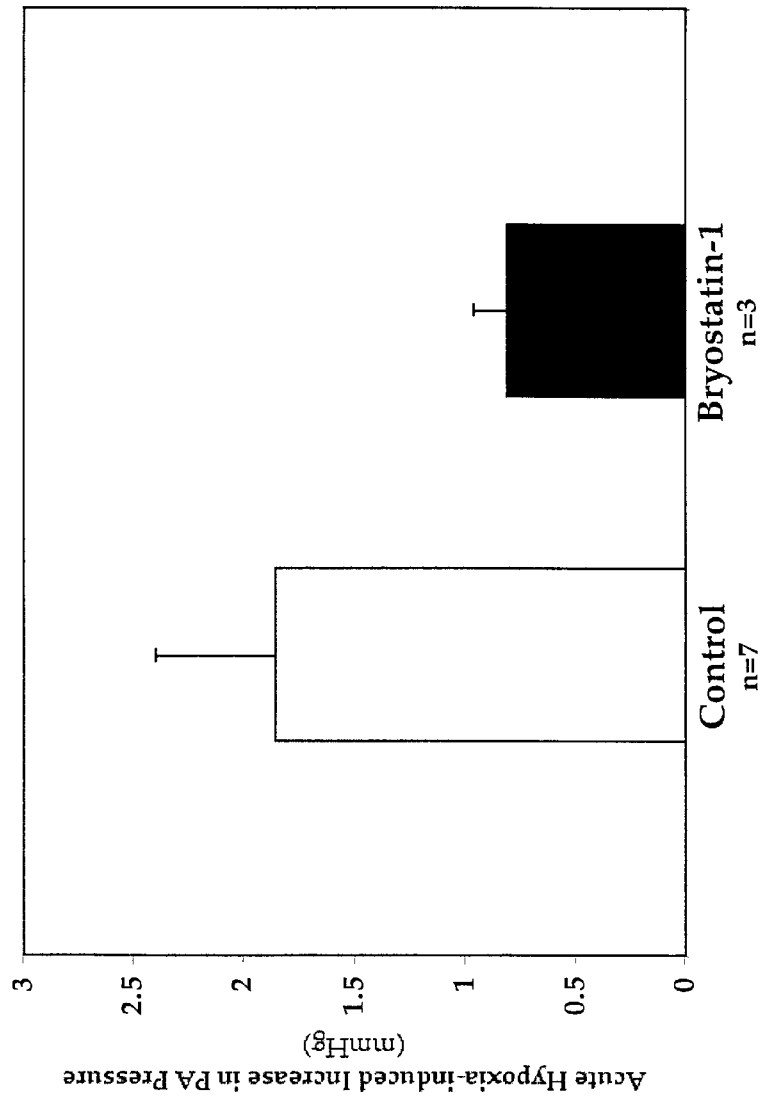

Figure 12: Preliminary data suggests that whole animal pretreatment with Bryostatin-1 blunts acute vasoconstrictor response to hypoxia. Four day pretreatment with bryostatin-1 at 33μg/kg/qd dose. Intact chest modified perfused lung preparation used. Hypoxic response determined from average of three or four successive acute challenges with 0% oxygen. N equals 3-7 adult ICR mice.

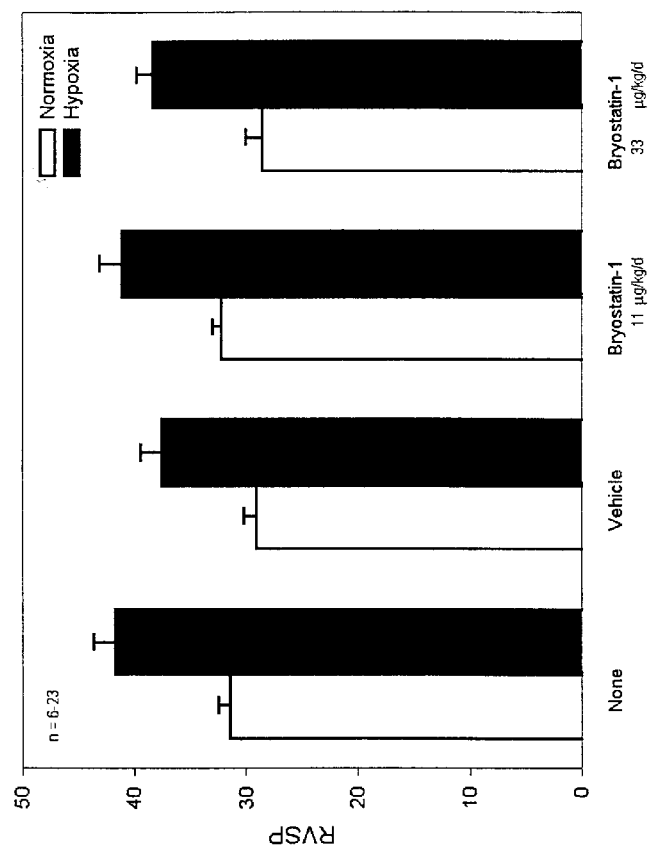

Figure 13: At the immediate end of the experimental protocol the hypoxia-induced increase in right ventricular systolic pressure (RVSP) did not appear to be attenuated by Bryostatin-1. RVSP is an index of pulmonary artery pressure. RVSP was measured in normoxic and hypoxic mice treated with nothing, vehicle (30% DMSO) or Bryostatin-1 at 11- or 33 μg/kg/d. Measurements were done at Denver altitude (5280 ft) in anesthetized, spontaneously breathing mice by percutaneous cardiac puncture. RVSP in hypoxic mice was measured immediately following removal from the hypobaric chamber. ( ☐ Normoxia, ■ Hypoxia). N=6-23 for all groups. One possible explanation for this was that drug delivery may have ended prematurely with a resulting transient increase in vascular tone.

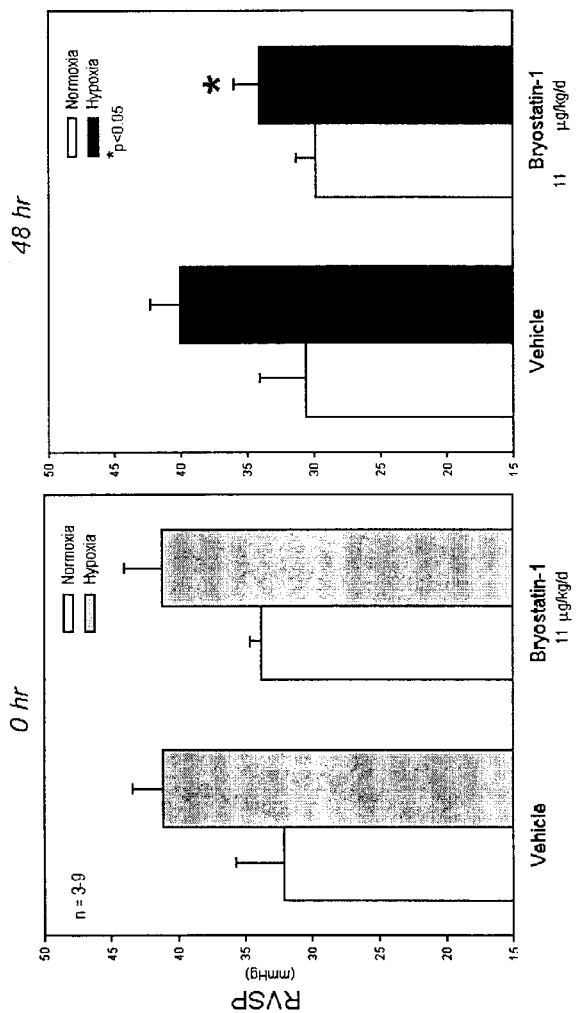

Figure 14: Demonstration of attenuating effect of Bryostatin-1 on RVSP when measurements are made after reintroduction to normoxia (Denver altitude). RVSP was measured in normoxic and hypoxic mice treated with vehicle (30% DMSO) or Bryostatin-1 at 11 µg/kg/d. Measurements were done at Denver altitude (5280 ft) in anesthetized, spontaneously breathing mice by percutaneous cardiac puncture. Hypoxic mice were reintroduced to Denver altitude for 0 vs. 48 hours before RVSP measurements were performed. A. Measurements done immediately out of hypobaric chamber (☐ ■ Vehicle, ☐ ■ Bryostatin-1 11 µg/kg/d). N=3-9. B. Measurements done 48 hr after reintroduction to Denver altitude (☐ ■ Vehicle, ☐ ■ Bryostatin-1 11 µg/kg/d). N=3-9 for all groups. *$p \leq 0.05$ as compared to vehicle-treated hypoxic group. This data together with morphometric analysis suggests that the reason for lack of difference in RVSP at immediate end of protocol may have been due to drug delivery issues (premature infusion pump emptying or loss of inhibitory effect between 4d ip dosing intervals).

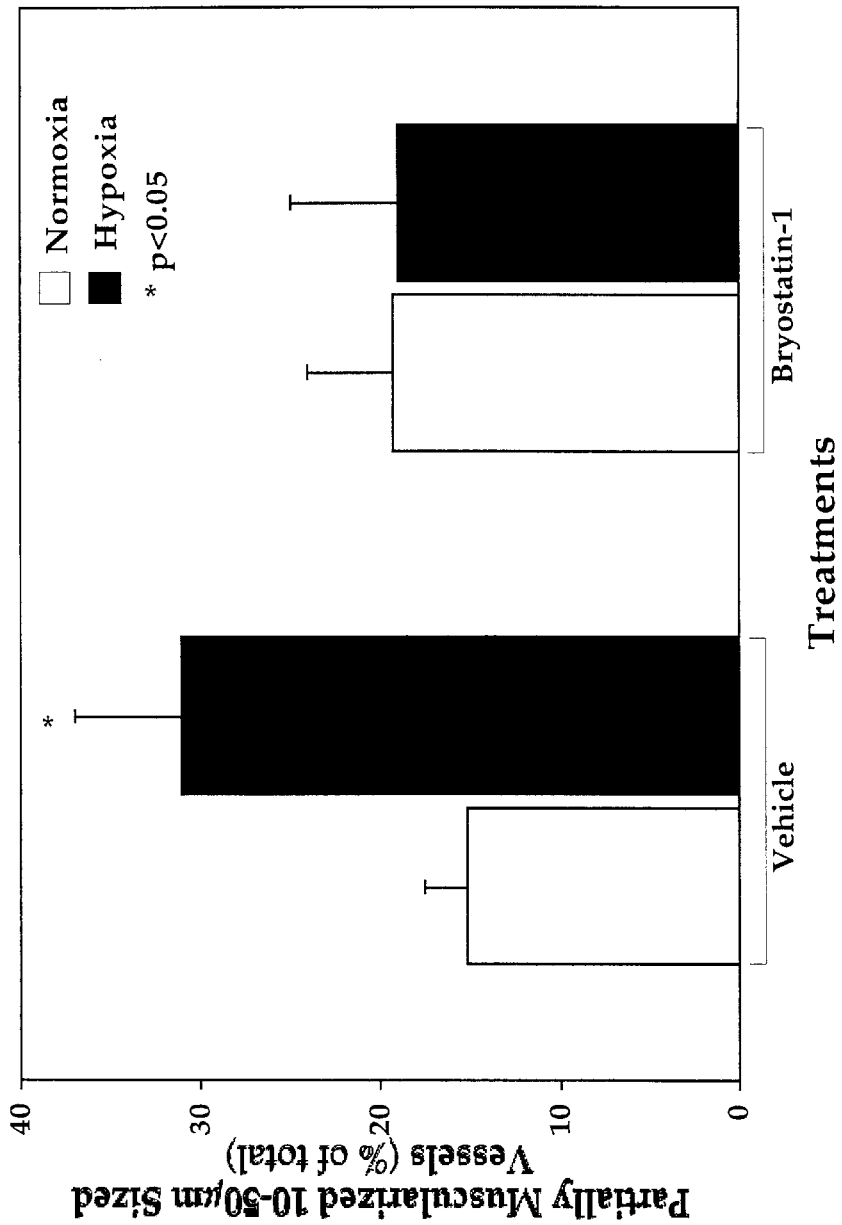

Figure15: Treatment with Bryostatin-1 appears to attenuate early murine pulmonary vascular remodeling in response to chronic hypoxia. Age matched adult male ICR mice. Paraformaldehyde/formalin fixation of lung tissue. Double staining for factor VIII to detect total number of vessels and alpha smooth muscle actin to identify subgroups that are partially muscularized (1-75% of circumference positive). At least 200 vessels analyzed per mouse lung using computerized digital imaging system. Blinded scoring. N=4-5 mice per treatment. Open bar (☐) groups exposed to Normoxia, defined as Denver altitude (5,280 ft) for 4 weeks. Black bar (■) groups exposed to Hypoxia (17,000 ft) for 4 weeks.

METHOD OF USING PKC INHIBITING COMPOUNDS TO TREAT VASCULAR DISEASE

CROSS REFERENCE TO RELATED APPLICATION

This application claims priority from U.S. Provisional Patent Application Ser. No. 60/130,916 filed on Apr. 23, 1999. The entire disclosure of the provisional application is considered to be part of the disclosure of the accompanying application and is hereby incorporated by reference.

GOVERNMENT GRANT

This invention was made with government support under a grant awarded by the National Heart, Lung, and Blood Institute, Grant No. PPGHL14985. The government has certain rights to this invention.

FIELD OF THE INVENTION

The present invention is directed to a method for treating pulmonary and systemic vascular diseases associated with cardiac hypertrophy, dysfunction, or failure, such method comprising administering effective amounts of a PKC antagonist to a patient suffering from one of such diseases. The methods may also be effective at directly treating airway and interstitial diseases of the lung that lead to the development of pulmonary hypertension. Other embodiments relate to particular formulations of bryostatin compounds formulated for particular diseases, as well as methods of using such compounds to treat patients having such diseases.

BACKGROUND OF THE INVENTION

Adult and neonatal pulmonary and systemic vascular disease is a common clinical problem. These vascular diseases include pulmonary and/or systemic hypertension, atherosclerosis, post-angioplasty re-stenosis, post-transplant vasculopathy, diabetic vasculopathy, peripheral vascular disease, vasculitis, and capillaritis. They are complicated by cardiac hypertrophy, dysfunction, or failure. These clinical problems characteristically include alterations in vascular structure, such as abnormalities in vessel wall thickness and/or vessel formation and/or obliteration, and alterations in vascular tone, such as abnormal contractile response to agonists. Myocardial hypertrophy, dysfunction, or failure are also often observed. These disease processes also cause important vascular cell responses in smooth muscle cells, adventitial fibroblasts, and endothelial cells that contribute to the disease process, including hypertrophy, proliferation, migration, matrix protein synthesis, permeability, and contraction. Inflammatory cell recruitment and activation is also though to be important in the pathogenesis of vascular disease.

Among these diseases is chronic hypoxic pulmonary hypertension (PHTN), which results from structural remodeling and abnormalities of vascular tone (Reeves and Herget, 1984; Haworth, 1993). The alteration in vascular structure results from changes in cellular hypertrophy, proliferation, apoptosis, differentiation, migration, permeability and matrix protein synthesis (Meyrick and Reid, 1979; Rabinovich, et al., 1981; Jones, et al., 1984; Stenmark, et al., 1987). The pulmonary hypertensive process has been observed in several species, including adult mice (Hales, et al., 1983; Klinger, et al., 1993; Steudel, et al., 1998; Fagan, et al., 1999).

The cellular and molecular mechanisms by which the pulmonary hypertensive process occurs are still poorly understood. However, it has been observed that protein kinase C (PKC) is involved in many of the vascular cell responses that contribute to the pulmonary hypertensive process (Komero, et al., 1991; Nishizuka, 1992; Haller, et al., 1994; Ways, et al., 1995). PKC is an important signal transduction pathway involving a family of at least 11 related intracellular kinases. One isozyme in particular, PKC-α, has been implicated in vascular cell responses to hypoxia (Goldberg, et al., 1997; Dempsey, et al., 1997, 1998; Xu, et al., 1997). On the basis of this assertion, as well as earlier studies, the PKC pathway has been presumed to be important in the pathogenesis of chronic hypoxic PHTN (Orton and McMurtry, 1990; Dempsey, et al., 1990, 1991; Xu, et al., 1997). Mechanisms that important here (like PKC) are also thought to play a critical role in other forms of PHTN, systemic vascular diseases, and various lung conditions like asthma, bronchiolitis, interstitial lung disease and lung injury.

It is, therefore, desirable to develop pharmacological strategies to attenuate chronic hypoxic pulmonary hypertension. One such strategy involves the PKC signal transduction pathway. One family of compounds that bind to PKC with high affinity is the bryostatins, a group of macrocyclic lactones isolated from marine bryozoans (Pettit et al., 1982; Kraft et al. 1986). In vitro, it has been found that bryostatin-1 inhibits cell growth and activity of isozymes of PKC, as well as inducing cell differentiation and apoptosis of a variety of transformed cell lines. Its effects on migration and contraction are unknown. Bryostatin-1 induces rapid inactivation and degradation of PKC in a cell-type-and isozyme-specific manner (Lee, et al., 1996, 1997; Blumberg, et al., 1997). In vivo, bryostatin-1 is known to accumulate in the lung in high concentrations. It is currently being tested in NCI-sponsored clinical trials for treatment of several types of malignancies (Zhang, et al., 1996; Caponigro, et al., 1997; Weitman et al., 1999).

SUMMARY OF THE INVENTION

In accordance with the present invention, bryostatin-1 has been tested in vitro in bovine pulmonary artery smooth muscle cells and in vivo in an adult murine model of vascular disease, specifically, chronic hypoxic pulmonary hypertension. The present invention relates to the discovery that bryostatin-1 can attenuate the development of chronic hypoxic pulmonary hypertension in adult ICR mice. The attenuating effects observed here on pulmonary vessels and the right ventricle of the heart are applicable to other types of pulmonary and systemic vascular and related disease. Other bryostatin derivatives could also have attenuating effects on these vascular disorders.

BRIEF DESCRIPTION OF THE DRAWINGS

FIG. 1 illustrates abnormalities in vascular tone and structure that lead to chronic hypoxic pulmonary hypertension with representative slides of bovine lung tissue.

FIG. 2 is a diagram illustrating PA SMC proliferative response to hypoxia.

FIG. 3 is a bar graph illustrating pretreatment with bryostatin-1 attenuating hypoxic growth of adult bovine pulmonary artery (PA) smooth muscle cells (SMC) in vitro.

FIG. 4 is a bar graph illustrating that Go-6976, like bryostatin-1, inhibits hypoxia-induced PA SMC proliferation. Go-6076 inhibits activity of PKC-α and β in this preparation.

FIG. 5 is a bar graph illustrating that bryostatin-1 induced degradation of PKC-α is time dependent in bovine PA SMC.

FIG. 6 is a bar graph illustrating the dose-dependent effect of bryostatin-1 on degradation of PKC-α and hypoxic growth in bovine PA SMC.

FIG. 7 illustrates a gel showing that pretreatment with bryostatin-1 for 4 hours induces selective degradation of PKC-α in adult bovine PA SMC.

FIG. 8 illustrates chronic treatment of mice with bryostatin-1 decreases PKC-α protein levels in whole lung homogenates.

FIG. 9 illustrates a bar graph showing hematocrit levels in response to chronic hypoxia and bryostatin-1 administration.

FIG. 10 illustrates a bar graph showing the effect of hypoxia, vehicle and bryostatin-1 on right ventricular (RV) hypertrophy.

FIG. 11 illustrates a bar graph showing that subgroup analysis reveals a more marked attenuating effect of bryostatin-1 on hypoxia-induced right ventricular (RV) hypertrophy in a larger subgroup of adult ICR mice.

FIG. 12 is a bar graph illustrating preliminary data showing whole animal pre-treatment with bryostatin-1 blunts acute vasoconstrictor response to hypoxia.

FIG. 13 illustrates a bar graph showing the effect of hypoxia, vehicle and bryostatin-1 on initial right ventricular systolic pressure (RVSP) measurements.

FIG. 14 illustrates a bar graph showing the effect of chronic hypoxia and bryostatin-1 on right ventricular systolic pressure measurements made 0 vs. 48 hours after reintroduction to normoxia (Denver altitude).

FIG. 15 illustrates a bar graph showing the effect of bryostatin-1 attenuating early murine pulmonary vascular remodeling in response to chronic hypoxia.

DETAILED DESCRIPTION OF THE PREFERRED EMBODIMENT

One aspect of the present invention relates to the specificity of bryostatin-like compounds with respect to cell type and PKC isozymes. In particular, bryostatin accumulates in lung tissue in high concentrations. It has been shown to inhibit cell growth and induces rapid inactivation and degradation of PKC. It binds to PKC with high affinity. The present inventor is the first to appreciate that bryostatin-1 will inhibit the hypoxic proliferative response in animals, and particularly mammals. For example, the inventor of the present invention is the first to appreciate that bryostatin-1 inhibits the hypoxic proliferative response of adult bovine PA SMC in vitro. Such inhibitory effect is mediated, at least in part, by inducing the degradation of PKC-α. The present inventor is also the first to appreciate that bryostatin-1 inhibits hypoxic growth and expression of selected PKC isozymes, in particular α-PKC, in vascular cells.

An effective agent for use in the present invention has one or more of the following characteristics: it upregulates growth, upregulates differentiation, upregulates apoptosis, down regulates contraction, down regulates migration and down regulates matrix protein synthesis. Agents having one or more of the above characteristics are potentially useful in decreasing vascular disease. Particularly preferred agents for use in the present invention include bryostatins which antagonize the signal transduction pathway important in vascular biology, such pathway including PKC.

Additional agents can be used in conjunction with the PKC antagonist described in the present invention, particularly bryostatin. In particular, combining PKC antagonists such as bryostatin with a second agent, such as tamoxifen, augments the results achieved using the PKC antagonist alone.

The method of the present invention can be used in any animal, and particularly, in any animal of the Vertebrate class, Mammalia, including, without limitation, primates, rodents, livestock and domestic pets. Preferred mammals to treat using the method of the present invention include humans.

The method of the present invention includes a step of administering an effective amount of a PKC antagonist, such as bryostatin or bryostatin derivatives (hereinafter collectively referred to as bryostatin, bryostatin-like compounds and/or PKC inhibitors or antagonists) to an animal that has, or is at risk of developing vascular diseases, including but not limited to chronic hypoxic pulmonary hypertension (CHPH), diabetes, ostheroscherosis, post-angioplasty, restenosis. According to the present invention, to inhibit vascular disease in an animal refers to inhibiting hypoxic growth and/or the expression of selected PKC isozymes, and in particular, α-PKC, due to the biological activity of bryostatin-like compounds. Inhibition of vascular disease according to the present invention can be accomplished by directly affecting the down-regulation of one or more $CA^{2+}$-dependent isozymes by agents having bryostatin biological activity.

A further aspect of the present invention relates to the selective nature of bryostatin on inhibition of hypoxic growth. The down regulating effect of bryostatin is isozyme selective as evidenced by the fact that no degradation of other $CA^{2+}$-dependent isozymes were expressed in adult cells nor were other $CA^{2+}$-dependent isozymes detected (i.e., δ,ε,ζ,ι,μ). Therefore, bryostatin inhibits hypoxic growth by a mechanism that is dependent upon PKC, and in particular, PKC-α. Reference to PKC-α should be understood to refer to all PKC. Bryostatin is therefore useful in attenuating abnormal SMC growth, both in vitro and in vivo.

As used herein, inhibition of vascular disease is defined herein as any measurable (detectable) reduction (i.e., decrease, down regulation, inhibition) of the biological activity of PKC. The biological activity or biological action of a bryostatin-like compound refers to any function(s) exhibited or performed by a naturally occurring form of a bryostatin compound as measured or observed in vivo (i.e., in the natural physiological environment of the compound) or in vitro (i.e., under laboratory conditions). According to the present invention, vascular disease is inhibited by directly inducing the proteolytic degradation of PKC. Preferably, vascular disease is inhibited by administering an agent including, but not limited to, an agent that binds to either and/or selectively degrades PKC and/or that interferes with the expression of PKC. Such an agent includes, but is not limited to bryostatin-like compounds, PKC antagonists and PKC antibodies.

Accordingly, the method of the present invention includes the use of a variety of agents (i.e., regulatory compounds) which, by acting to inhibit PKC activity, undesired hypoxic growth and vascular disease is reduced in an animal. Agents useful in the present invention include, for example, compounds, nucleic acid molecules, antibodies, and compounds that are products of rational drug design (i.e., drugs). Such agents are generally referred to herein as bryostatin-like compounds and include PKC degeneration compounds, bryostatin-1 and active moieties which form a portion of bryostatin that are effective in inhibiting, for example, the action of PKC-α. According to the present invention, a PKC inhibitor is any agent or mimetic which inhibits, either by direct inhibition or competitive inhibition, the expression and/or biological activity of PKC and includes agents which act similar to bryostatin.

As used herein, the term "mimetic" is used to refer to any peptide or non-peptide compound that is able to mimic the biological action of a naturally occurring PKC antagonist, such as bryostatin, often because the mimetic has a basic structure that mimics the basic structure of the naturally occurring compound and/or has the salient biological properties of the naturally occurring compound. Mimetics can include, but are not limited to: peptides that have substantial modifications from the prototype such as no side chain similarity with the naturally occurring compound (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

PKC inhibiting agents as referred to herein include, for example, compounds that are products of rational drug design, natural products, and compounds having partially defined PKC regulatory properties. A PKC regulatory agent can be a bryostatin-based compound, a carbohydrate-based compound, a lipid-based compound, a nucleic acid-based compound, a natural organic compound, a synthetically derived organic compound, an antibody, or fragments thereof. An effective PKC inhibitor of the present invention preferably has a structural configuration which enables biological associations with PKC that are effective to inhibit PKC activity. In one embodiment, PKC regulatory agents of the present invention include drugs, including peptides, oligonucleotides, carbohydrates and/or synthetic organic molecules which regulate the production and/or function of PKC. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies,* Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Another compound useful in the method of the present invention includes a fusion protein that includes at least one PKC antagonist (or a homologue or peptide mimetic thereof) attached to one or more fusion segments. Suitable fusion segments for use with the present invention include, but are not limited to, segments that can: enhance a protein's stability; act as an enhancer or inhibitor of the biological activity of a PKC antagonist; and/or assist with the purification of a PKC antagonist (e.g., by affinity chromatography). A suitable fusion segment can be a domain of any size that has the desired function (e.g., imparts increased stability, imparts increased biological activity to a protein, and/or simplifies purification of a protein). Fusion segments can be made susceptible to cleavage in order to facilitate recovery of an isolated protein comprising a PKC antagonist.

While the present invention, in one embodiment, is directed to the use of PKC antagonist compounds alone, it can also be used in combination with other agents, and particularly other vascular disease treating agents.

In accordance with the present invention, acceptable protocols to administer an agent including the route of administration and the effective amount of an agent to be administered to an animal can be accomplished by those skilled in the art. An agent (e.g., bryostatin-1) of the present invention can be administered in vivo or ex vivo. Suitable in vivo routes of administration can include, but are not limited to, oral, nasal, inhaled, topical, intratracheal, transdermal, rectal, and parenteral routes. Preferred parenteral routes can include, but are not limited to, subcutaneous, intradermal, intravenous, intramuscular, and intraperitoneal routes. Preferred topical routes include inhalation by aerosol (i.e., spraying) or topical surface administration to the skin of a mammal. An agent may be administered by nasal, inhaled, intratracheal, topical, or intravenous routes. Ex vivo refers to performing part of the administration step outside of the patient. Ex vivo methods are particularly suitable when the cell to which the agent is to be delivered can easily be removed from and returned to the patient.

According to the method of the present invention, an effective amount of a agent that inhibits PKC (also referred to herein simply as "an agent") to administer to an animal comprises an amount that is capable of reducing vascular disease without being toxic to the mammal. An amount that is toxic to an animal comprises any amount that causes damage to the structure or function of an animal (i.e., poisonous).

A suitable single dose of a PKC inhibitory agent to administer to an animal is a dose that is capable of reducing or preventing vascular disease in an animal when administered one or more times over a suitable time period. For example, a suitable single dose of an agent comprises a dose that improves CHPH by a doubling dose of a provoking agent or improves the static respiratory function of an animal. A preferred single dose of an agent comprises between about 0.01 microgram×kilogram$^{-1}$ and about 10 milligram×kilogram$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. A particularly preferred single dose of an agent comprises between about 0.1 milligram×kilogram$^{-1}$ and about 5 milligram×kilogram$^{-1}$ body weight of an animal, if the an agent is delivered by aerosol. Another particularly preferred single dose of an agent comprises between about 0.1 microgram×kilogram$^{-1}$ and about 10 microgram×kilogram$^{-1}$ body weight of an animal, if the agent is delivered parenterally.

In one embodiment, the PKC-inhibitory agent is administered with a pharmaceutically acceptable carrier, which includes pharmaceutically acceptable excipients and/or delivery vehicles, for administering the agent to a patient (e.g., a liposome delivery vehicle). As used herein, a pharmaceutically acceptable carrier refers to any substance suitable for delivering a PKC-inhibitory agent useful in the method of the present invention to a suitable in vivo or ex vivo site. Preferred pharmaceutically acceptable carriers are capable of maintaining an agent of the present invention in a form that, upon arrival of the agent in the animal, the agent is capable of interacting with its target, such that vascular disease is reduced or prevented. Suitable excipients of the present invention include excipients or formularies that transport or help transport, but do not specifically target an agent to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into an animal. As used herein, a controlled release formulation comprises an agent of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. As discussed above, a delivery vehicle of the present invention can be modified to target to a particular site in a patient, thereby targeting and making use of a PKC-inhibitory agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is herein referred to as a "delivery vehicle." Delivery vehicles of the present invention are capable of delivering a formulation, including a PKC-inhibitory agent to a target site in a mammal. Additional delivery vehicles can include DMSO/phosphate buffered saline, PET diluent (for example, used by NCI for human trials), etc. A "target site" refers to a site in a mammal to which one desires to deliver a therapeutic formulation. For example, a target site can be any cell which is targeted by direct injection or delivery using liposomes, viral vectors or other delivery vehicles, including ribozymes. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a mammal. Suitable modifications include manipulating the chemical formula of the lipid portion of the delivery vehicle and/or introducing into the vehicle a compound capable of specifically targeting a delivery vehicle to a preferred site, for example, a preferred cell type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One preferred delivery vehicle of the present invention is a liposome. A liposome is capable of remaining stable in an animal for a sufficient amount of time to deliver an agent described in the present invention to a preferred site in the animal. A liposome, according to the present invention, comprises a lipid composition that is capable of delivering an agent described in the present invention to a particular, or selected, site in a mammal. A liposome according to the present invention comprises a lipid composition that is capable of fusing with the plasma membrane of the targeted cell to deliver an agent into a cell. Suitable liposomes for use with the present invention include any liposome. Preferred liposomes comprise liposomes having a polycationic lipid composition and/or liposomes having a cholesterol backbone conjugated to polyethylene glycol. Also, the agents of the present can be delivered in a intra-dermal fashion.

In another embodiment, the method of the present invention is useful for treating any animal for the purposes of ameliorating vascular disease. The phrase, "to treat" a condition such as vascular disease in a patient refers to reducing, ameliorating or preventing the condition in a patient that suffers from the condition or is at risk of acquiring the condition. Therefore, in one embodiment of the present invention, "to treat" a disorder can also mean "to prevent" the disorder in a patient. Preferably, the condition, or the potential for developing the condition, is reduced, optimally, to an extent that the patient no longer suffers from the condition or to decrease the discomfort and/or altered functions and detrimental conditions associated with the disease. More particularly, "to treat" a condition associated with vascular disease includes the administration of PKC antagonist compounds as disclosed herein to prevent the onset of the symptoms or complications of such a condition, to alleviate the symptoms or complications, or to eliminate the condition.

The methods disclosed herein can also be used in conjunction with other methods related to the treatment of vascular disease or related conditions, including, but not limited to, coadministration of another vascular disease treating agent or compound.

The present invention also includes a formulation that reduces or prevents vascular disease in an animal. The formulation comprises: (a) an inhibitor of PKC selected from the group of: bryostatin, an agent which binds to a bryostatin receptor; a bryostatin-like compound having PKC (and particularly PKC-α) degradative capabilities, and an anti-inflammatory agent suitable for reducing CHPH in an animal that has, or is at risk of developing, CHPH.

Yet another embodiment of the present invention relates to a method to identify a compound that reduces or prevents vascular disease. Such a method includes the steps of: (a) contacting a putative regulatory compound with a cell that expresses PKC wherein in the absence of the putative regulatory compound, PKC can be expressed and is biologically active; (b) detecting whether the putative regulatory compound inhibits PKC expression or activity by the cell; and, (c) administering the putative regulatory compound to a non-human animal in which vascular disease can be induced and identifying animals in which vascular disease is reduced or prevented as compared to in the absence of the putative regulatory compound. A putative regulatory compound that inhibits PKC expression or activity and that reduces or prevents vascular disease in the non-human animal is indicated to be a compound for reducing or preventing vascular disease.

In this method, the step (b) of detecting can include, but is not limited to, a method selected from the group of measurement of PKC biological activity associated with the cell. Such methods of detecting an interaction of a ligand with a receptor, including the interaction of a ligand and PKC, are known in the art, and include immunoblots, phosphorylation assays, kinase assays, immunofluorescence microscopy, RNA assays, immunoprecipitation, and other biological assays.

As used herein, the term "putative" refers to compounds having an unknown or previously unappreciated regulatory activity in a particular process. As such, the term "identify" is intended to include all compounds, the usefulness of which as a regulatory compound of PKC expression or biological activity for the purposes of reducing vascular disease is determined by a method of the present invention.

The above-described methods for identifying a compound of the present invention include contacting a test cell or a cell lysate with a compound being tested for its ability to bind to and/or regulate the activity of PKC. For example, test cells can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micro-nutrients.

The above described methods, in one aspect, involve contacting cells with the compound being tested for a sufficient time to allow for interaction of the putative regulatory compound with PKC. The period of contact with the compound being tested can be varied depending on the result being measured, and can be determined by one of skill in the art. For example, for binding assays, a shorter time of contact with the compound being tested is typically suitable, than when activation is assessed. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. It will be recognized that shorter incubation times are preferable because compounds can be more rapidly screened. A preferred incubation time is between about 1 minute to about 48 hours.

The conditions under which the cell or cell lysate of the present invention is contacted with a putative regulatory compound, such as by mixing, are any suitable culture or assay conditions and includes an effective medium in which the cell can be cultured or in which the cell lysate can be evaluated in the presence and absence of a putative regulatory compound. As may be appreciated, putative regulatory compounds preferably share structural characteristics with bryostatin and/or incorporate bryostatin as part of the compound.

Finally, a putative regulatory compound of the present invention can be evaluated by administering putative regulatory compounds to a non-human test animal and detecting whether the putative regulatory compound reduces vascular disease in the test animal. Animal models of disease are invaluable to provide evidence to support a hypothesis or justify human experiments. For example, mice have many proteins which share greater than 90% homology with corresponding human proteins. Preferred modes of administration, including dose, route and other aspects of the method are as previously described herein for the therapeutic methods of the present invention. The test animal can be any suitable non-human animal, including any test animal described in the art for evaluation of vascular disease.

Compounds identified by any of the above-described methods can be used in a method for the reduction or prevention of vascular disease as described herein.

It will be understood that the method and compounds as set forth in the present invention call for use in preventing, attenuating and reversing vascular disease. The present invention is therefore useful in ameliorating abnormalties of vessel formation for obliteration that may be the consequence of any particular vascular disease. It should also be appreciated that the agents used in the present invention, including not but not limited to bryostatin, and particularly bryostatin-1 and its derivatives, are useful to treat various pathogenesis of various forms of pulmonary hypertension, systemic vascular disease, and other forms of injury, inflammation and abnormal growth in the lung. The present invention is therefore useful for all forms of idiopathic primary and secondary (including hypoxic) pulmonary hypertension at rest or with exercise. In addition, the present invention is useful for treating earlier forms of vascular disease prior to the detectability of hypertension wherein only subtle structural changes or vascular disfunction may be apparent, resulting, for example, in hypoxemia out of proportion to pulmonary function testing. One particular use of the present invention is for the treatment of non-diabetic peripheral vascular disease. In addition to the above listed target cells to which the present invention relates, one will also understand that the present invention is useful in ailments involving inflammatory cell migration, recruitment, retention and activation in lung tissue. Various agents of the present invention, including bryostatin and bryostatin-1 in particular, are believed to have therapeutic effects on such cells. Such agents are also believed beneficial to affect various inflammatory states in view of the fact that inflammation is an important stimulus for vascular remodeling.

The PKC antagonist of the present invention, including bryostatin and in particular, bryostatin-1 and its analogs, are useful in the treatment of a variety of diseases including asthma and many forms of bronchiolitis, all forms of acute and chronic interstitial lung disease, injuries to lung tissues, and as a chemo-preventative agent for lung cancer (useful in the prevention of carcinogenisis as opposed to a treatment for transformed cells, such as lung cancer cells). While not bound by theory, the present inventor believes that because bryostatin-1 mimics and/or exceeds effects of heparin on the growth inhibition of vascular cells, and because heparin has been found in experimental systems to be useful in several of the above-referenced disease states and conditions, agents of the present invention are believed to have beneficial effects on the same or similar conditions as have been previously treated with heparin.

It should further be appreciated that the effects of the PKC antagonists as disclosed in the present invention have complex effects. As noted above, although the PKC antagonists, such as bryostatin, act as an initial activator of PKC, it can later inactivate and induce the degradation of various PKC isozymes. Thus, the effects of agents used in the present invention can be cell type specific, species specific and dose and time dependent. Due to the inter-relatedness and "cross talk" between PKC isozymes with other kinase cascades, and thus the regulation of various genes, the effects of bryostatin-like compounds in cells, organs and species are of significant breadth. Moreover, bryostatin compounds are believed to have effects that are not dependent upon PKC, but which are also believed to be clinically useful in treating one or more of the above-referenced disease states.

Bryostatin has various effects, as generally discussed above, on various isozymes of PKC. For example, PKC-α is very susceptible to degradation and is useful in testing the effects of bryostatin analogs in cell culture and in whole animal models. Bryostatin also induces degradation of PKC-$β_μ$ and given this isozymes importance in growth processes, bryostatin analogs can be used to effect such growth. PKC-β is less susceptible to degradation, but is also believed to be important in growth. At high doses of bryostatin, PKC-δ activates and protects such isozyme from degradation. At a low dose of bryostatin, however, it is believed that PKC-δ is degraded. The role of PKC-δ in vascular disease is believed to be growth inhibitory and pro-apoptotic and thus, the activation of such isozyme is believed to be beneficial. PKC-ε is believed to be important in contraction and growth and is susceptible to degradation by bryostatin in some cell systems.

With respect to various bryostatin analogs, one of skill in the art will understand that bryostatin analogs can be created in view of the structural analysis and rational design possibilities emanating from work directed to the binding properties of bryostatin-1, phorbol ester (PMC) and diacylglycerol to recombinant PKC-α. Indeed, PKC activation is believed to occur when one activator binds to a low affinity (DAG>phorbol>bryo) site alosterically promoting binding of a second activator to a high affinity (bryo>phorbol>DAG) site resulting in enhanced activity. Thus, an effective PKC antagonist of the present invention can be designed to bind to either one of the activator sites mentioned above in order to enhance and/or decrease activity, as desired. Other strategies for the design of novel ligands with bryostatin-like activities may be gleaned from the fact that bryostatin-1, at high doses, acts to protect PKC-δ from down-regulation induced by PMC. Site directed mutagenesis has been used to determine that the second cysteine-rich region of PKC-δ is important in binding phorbol esters and bryostatin-1. Site directed mutagenesis also evidences the importance of C1a and C1b phorbal esther binding domains of PKC-δ. Indeed, different selectivity of ligands has been found to have correlations with tumor promoting activities. Thus, the importance of C1a and C1b binding domains is that down-regulation by bryostatin is possible in a dose dependent protection fashion. C1 domain peptides that have been generated for all PKC isozymes can be used in the identification of desired bryostatin analogs. For example, preferred bryostatin analogs can be designed to retain putative recognition domains and can be simplified through deletions and/or modifications of C1–C14 spacer domains. The stereochemistry of C3 hydroxyl groups is believed to be important in the protection of bryostatin analogs having desired binding capabilities.

Finally, as one of ordinary skill in the art will appreciate, the various PKC antagonists and bryostatin analogs of the present invention can be used in combination with other agents to potentiate therapeutic effects, for example, by increasing apoptosis, decreasing growth, etc. Such other agents include estrogen-like derivatives like tamoxifen; chemotherapeutic agents like paclitaxel, vincristine and cisplatin; antitubulin agents like dolastatin 10 and amistatin PE; steroid hormones/vitamins like 1α, 25 dihydroxyvitamin D3; other PKC inhibitors like CGP41251 and staurosporine; immune modulators like interferon-γ; vasodilators like ACE inhibitors, calcium channel blockers, NEP inhibitors, ET antagonists and prostacyclin derivatives and other drugs that may exert attenuating effects on vascular (or airway or interstitial structure) structure like heparin.

Applicants incorporate by reference in their entireties the following U.S. patents to supplement the present written description of the present invention: U.S. Pat. Nos. 5,981,569; 5,886,195; 5,792,771; and 5,763,441. Additional patents are incorporated herein by reference which disclose various PKC modulators and inhibitors which, as one of ordinary skill in the art will recognize, could be used in the method of the present invention in place of and/or in conjunction with bryostatin compounds or bryostatin derivatives: U.S. Pat. Nos. 5,189,046; 5,744,460 and 5,648,238.

The following experimental results are provided for purposes of illustration and are not intended to limit the scope of the present invention.

Example 1

The effect of bryostatin-1 on hypoxic growth and PKC isozyme expression in adult bovine pulmonary artery smooth muscle cells was tested. Hypoxic growth was induced by priming with the PKC activator, 10 nM PMA. Proliferative response was measured by $^3$H-thymidine incorporation and cell counts. Isozyme expression was measured by Western blot. Pretreatment with 10 to 100 nM bryostatin-1 for 4 or 24 hr inhibited the proliferative response to PMA and hypoxia (3% oxygen). Inhibitors of the $Ca^{2+}$-dependent isozymes of PKC (1.0 μM GF1092203X and Go6976) had similar anti-proliferative effects. This data suggested that bryostatin-1 might be down-regulating one or more of the $Ca^{2+}$-dependent isozymes in pulmonary artery smooth muscle cells. Therefore, the differential effects of bryostatin-1 on PKC isozyme expression were determined. bryostatin-1 (100 nM) rapidly induced the proteolytic degradation of PKC-α in smooth muscle cells, with degradation first detectable by 1 hour and complete by 24 hours. The threshold concentration to induce degradation was 10 nM, with a maximal effect at 50 to 100 nM. This same amount of bryostatin had been found to inhibit hypoxic growth. The down-regulating effect of bryostatin-1 was isozyme-selective. No degradation of the other $Ca^{2+}$-dependent isozyme expressed in these adult cells (βI) or five other $Ca^{2+}$-independent isozymes was detected (δ,ε,ζ,ι,μ). These results suggest that bryostatin-1 inhibits hypoxic growth of PA SMC by a mechanism that is dependent on PKC-α and may be useful in attenuating abnormal smooth muscle cell growth both in vitro and in vivo. See L. J. Ruff and E. C. Dempsey, "BRYOSTATIN-1 ATTENUATES HYPOXIC GROWTH OF BOVINE PULMONARY ARTERY SMOOTH MUSCLE CELLS IN VITRO," FASEB J 12:A339, 1998.

Example 2

Bryostatin-1 was tested in a murine model of chronic hypoxic PHTN. Adult ICR mice were exposed to normoxia (N) (5,200 ft, Denver altitude) or hypoxia (H) (18,000 ft) for 4 weeks and received either no treatment (n=15–20), vehicle (DMSO; n=8), or bryostatin-1 at 11 or 33 μg/kg/d (n=13 and 7–10, respectively), delivered intraperitoneally. Hematocrit (Hct [%]), RV/LV+S, and RV systolic pressure (RVSP [mmHg]) were measured under normoxic conditions at 0 or 48 hr following removal from chamber. The results are shown in Table I. Chronic hypoxia caused an increase in Hct which was unchanged by vehicle or bryostatin-1. Hypoxia induced a rise in RV/LV+S and in RVSP. Initial (0 hour) measurements of RVSP following hypoxia in vehicle and drug treated groups were not different. However, when the measurements were made 48 hours later, an attenuating effect of bryostatin-1 on the hypoxia-induced increase in RVSP was detected. In conclusion, bryostatin-1 had attenuating effects in an adult murine model of chronic hypoxic pulmonary hypertension and is believed to be a useful pharmacological tool for the treatment this important clinical problem.

TABLE I

Effects of hypoxia on hematocrit, RV hypertrophy, and RVSP.

|  |  | No treatment (n = 5–20) | DMSO vehicle (n = 8) | bryostatin-1 11 μg/kg/d (n = 13) | bryostatin-1 33 μg/kg/d (n = 6–10) |
|---|---|---|---|---|---|
| Hematocrit, % |  | 39 ± 1 | 36 ± 2 | 35 ± 1 | 38 ± 4 |
|  | N | 51 ± 1 | 49 ± 1 | 48 ± 1 | 50 ± 3 |
|  | H |  |  |  |  |
| RV hypertrophy (RV/LV + S), *p < .05 |  | 0.29 ± 0.02 | 0.25 ± 0.02 | 0.28 ± 0.01 | 0.26 ± 0.06 |
|  | N | 0.41 ± 0.02 | 0.02 | 0.36 ± 0.02 | 0.34 ± 0.05 |
|  | H |  | 0.40 ± 0.02 |  |  |
| RVSP, 0 hours |  |  |  |  |  |
|  | N | 31 ± 1 |  |  |  |
|  | H | 42 ± 2 |  |  |  |
| RSP, 48 hours, *p < .05 |  |  | 31 ± 3 | 30 ± 2 |  |
|  | N |  | 40 ± 2 | 34 ± 2 |  |
|  | H |  |  |  |  |

See L Ruff, KE Grever, KA Fagan, IF McMurtry, AS Kraft, GR Pettit, and EC Dempsey, "ATTENUATING EFFECTS OF BRYOSTATIN-1 IN AN ADULT MURINE MODEL OF CHRONIC HYPOXIC PULMONARY HYPERTENSION," Abstract from American journal of respiratory and critical care medicine, Vol. 159, A163, March, 1999.

Based on these results, bryostatin compounds are shown to be useful in preventing, attenuating, and/or reversing abnormalities in cardiovascular structure and function.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for treating pulmonary and systemic vascular diseases associated with cardiac hypertrophy, dysfunction, or failure, the method comprising administering an effective dose of a PKC antagonist to a patient suffering from one of such diseases wherein the PKC antagonist is selected from bryostatin derivatives.

2. The method of claim 1 wherein the PKC antagonist is bryostatin-1.

3. The method of claim 1, wherein the disease is selected from pulmonary and/or systemic hypertension, atherosclerosis, post-angioplasty re-stenosis, post-transplant vasculopathy, diabetic vasculopathy, vasculitis, and capillaritis.

4. The method of claim 1, wherein the disease is characterized by alterations in at least one property selected from vascular structure and vascular tone.

5. The method of claim 4, wherein the alterations in vascular structure are selected from abnormalities in vessel wall thickness and vessel formation.

6. The method of claim 1, where in the disease is associated with myocardial hypertrophy, dysfunction, or failure.

7. The method of claim 1, wherein the disease is idiopathic pulmonary hypertension.

8. The method of claim 1, wherein the disease is chronic hypoxic pulmonary hypertension.

9. The method of claim 1, wherein the disease includes at least one cellular process which is aggravated or caused by hypoxia.

10. The method of claim 1, wherein the disease includes at least one cellular process involving abnormal PKC activity.

11. The method of claim 1, wherein the disease includes at least one cellular process involving abnormal PKC isozymes.

12. The method of claim 1, wherein the disease includes at least one cellular process involving abnormal PKC-α activity.

13. The method of claim 1, wherein the patient is murine.

* * * * *